United States Patent [19]

Laforest et al.

[11] 4,259,509

[45] Mar. 31, 1981

[54] 2-METHYL-2-PHENOXY-PROPIONIC ACID DERIVATIVES, PROCESS FOR THEIR PREPARATION AND THERAPEUTICAL APPLICATIONS THEREOF

[75] Inventors: Jacqueline Laforest, Vincennes; Jacqueline Bonnet, Vichy; Pierre Bessin, Chilly-Mazarin, all of France

[73] Assignee: Albert Rolland S.A., Paris, France

[21] Appl. No.: 874,479

[22] Filed: Feb. 2, 1978

[30] Foreign Application Priority Data

Feb. 14, 1977 [FR] France .............................. 77 04110
Dec. 21, 1977 [FR] France .............................. 77 38633

[51] Int. Cl.³ .................. C07D 307/52; C07D 333/22
[52] U.S. Cl. .................................. 549/77; 260/347.3; 260/347.4; 424/275; 424/285
[58] Field of Search .................... 260/332.2 A, 347.3, 260/347.4; 549/79, 77

[56] References Cited

U.S. PATENT DOCUMENTS 4,017,632 4/1977 Thuillier et al. ..................... 424/285
4,072,705 2/1978 Mieville ........................... 260/347.2

FOREIGN PATENT DOCUMENTS 2300552 9/1976 France.

OTHER PUBLICATIONS

Patai, Saul, "The Chemistry of the Carbonyl Group," Interscience Publ. (1966), pp. 199-201.
Grob, David et al., "Oximes for Anticholinesterase Intoxications," Modern Medicine (1958), vol. 26, No. 20, pp. 180-185, see Chemical Abstracts, vol. 53 #2480g.
Pham-Huu-Chanh et al., "Pharmacology of Oxime Derivatives: . . . ", Therapie (1970), vol. 25, No. 3, pp. 539-552, See Chemical Abstracts (1970), vol. 73, #64,865a.

Primary Examiner—Natalie Trousof
Assistant Examiner—L. Hendriksen

Attorney, Agent, or Firm—Young & Thompson

[57] ABSTRACT

This invention relates to compounds having the formula:

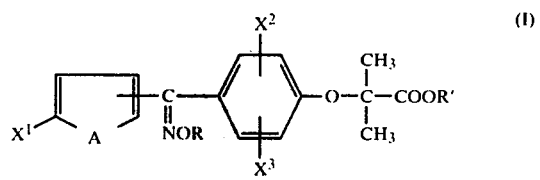

which represents the isomer Z, the isomer E or the mixture of both stereoisomers of the oximino group and in which:

A represents O or S, $X^1$ represents a halogen atom, a hydrogen atom or a methyl group, R represents a hydrogen atom or a $C_{1-5}$ alkyl group, $X^2$ and $X^3$, which may be the same or different, represent each a hydrogen atom, a halogen atom or a $C_{1-5}$ alkyl group, and R' represents a hydrogen atom or a $C_{1-5}$ alkyl group, and the group

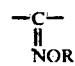

is at 2- or 3-position on the heterocycle, and the salts of acids of the formula (I) with physiologically acceptable bases, and the compounds which are metabolically converted to compounds of the formula (I).

Said compounds are therapeutically useful, typically as hypocholesterolemic, hypolipemic and uricosuric agents.

5 Claims, No Drawings

2-METHYL-2-PHENOXY-PROPIONIC ACID DERIVATIVES, PROCESS FOR THEIR PREPARATION AND THERAPEUTICAL APPLICATIONS THEREOF

This invention relates to new 2-methyl-2-phenoxy-propionic acid derivatives, to a process for their preparation and to their therapeutic applications. More particularly, this invention concerns oximes of 2-methyl-2(thenoyl- or furoyl-phenoxy)-propionic acids, and also of esters and salts thereof, a process for their preparation and their therapeutic applications, typically as hypocholesterolemic (or hypocholesterolemia-inducing), hypolipemic (or hypolipemia-inducing) and uricosuric (or hypouricemia-inducing) agents.

U.S. Pat. No. 4,072,705 discloses 2-methyl-2-phenoxy-propionic acids and, more particularly, 2-methyl-2(thenoyl- or furoyl-phenoxy)-propionic acids. Said compounds are described as having a hypocholesterolemic and hypolipemic activity.

This invention relates to 2-methyl-2-phenoxy-propionic acid derivatives having the formula:

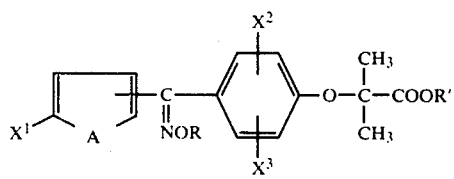

which formula represents the isomer Z, the isomer E or the mixture of both the stereoisomers of the oximino group, and in which:
A represents O or S,
$X^1$ represents a halogen or hydrogen atom, or a methyl group,
R represents a hydrogen atom or a $C_{1-5}$ alkyl group,
$X^2$ and $X^3$, which may be the same or different, represent each a hydrogen or halogen atom, or a $C_{1-5}$ alkyl group, and
R' represents a hydrogen atom or a $C_{1-5}$ alkyl group, the group

is at 2- or 3-position of the heterocycle,
and to the salts of acids of the formula (I) with physiologically acceptable bases, and also to the compounds which are metabolically converted to compounds of the formula (I).

The salts are typically those formed with physiologically acceptable alkali metal hydroxides and organic bases.

According to the invention, the compounds of the formula (I) are useful as active ingredients of new therapeutic compositions, typically administrable in the preventive or curative treatment of cardiovascular diseases. Indeed, such oximes possess a particularly valuable hypocholesterolemic and hypolipemic activity with respect to conventional hypocholesterolemic agents and to ketones of related formula some of which are disclosed in above-mentioned patent: the therapeutic index of oximes of the formula (I) is surprisingly markedly superior to that of the corresponding ketones, and this fact is all the more important as the therapeutic use of such drugs generally involve extended administration thereof: at comparable toxicity levels, determined from the $LD_{50}$ in mice, the minimum active dosage in the case of oximes is markedly lower than that of the ketones, while the activities of the latters are comparable with that of ethyl 4-chloro-phenoxy-isobutyrate (Clofibrate), a hypocholesterolemic agent commonly used in human therapeutics; in addition, most said oximes, and more particularly the acid derivatives and the salts thereof, possess an uricosuric activity which is highly useful in the treatment of gout and of cardiovascular diseases in which hyperuricemia is a substantial risk factor.

From the standpoint of the overall activity, a preferred class of the compounds of the formula (I) is that in which R is a $C_{1-5}$ alkyl group, and more particularly that in which $X^2$ and $X^3$ are hydrogen atoms.

This invention relates also to a process for the preparation of compounds of the formula (I), comprising reacting a ketone of the formula (II)

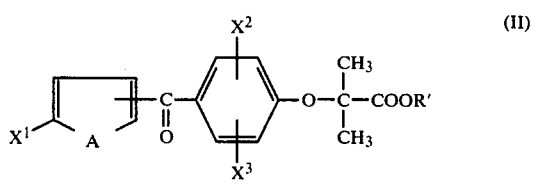

in which $X^1$, A, $X^2$, $X^3$ and R' have the above-defined meanings, with a hydroxylamine $H_2NOR$ optionally as a salt thereof, within a solvent.

Useful solvents include alcohols, aqueous alcohols, ether oxides, basic solvents such as pyridine, or mixtures thereof.

If desired, the reaction may be effected in the presence of a base such as an alkali or alkaline-earth metal acetate, carbonate or hydroxide, or of pyridine and its analogs.

The resulting material is a mixture of both stereoisomers of the oxime, in relative amounts which are dependent on the nature of the ketones and on the procedure used for the oximation.

If required, the mixture may be enriched in one of the isomers, by action of a hydrohalic acid in anhydrous medium, optionnally under the/action of photons, which are known isomerization conditions. Separation of the two isomers may be effected by recrystallization or chromatography.

When R'=alkyl, the oximation may, if required, be followed by alkaline hydrolysis of the ester in alcohol or aqueous-alcoholic solution. When R'=H, the oximation may, if required, be followed by conversion to the salt form.

The compounds of the formula (II) may be prepared by reacting a compound of the formula (III):

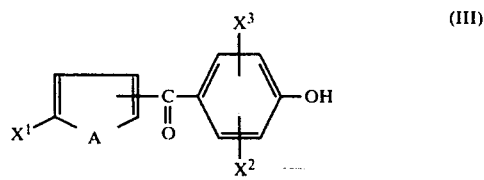

in which A, $X^1$, $X^2$ and $X^3$ have the above-mentioned meanings, with a halogen derivative of the formula (IV):

(IV)

in which Hal is halogen, typically bromine, and R' has the above-defined meaning, and more particularly ethyl α-bromoisobutyrate, within an aprotic polar solvent such as dimethyl formamide, dimethyl sulfoxide, or within an alcohol, dioxan or a ketone and in the presence of a base such as an alkali metal carbonate or hydroxide; and, if desired, to obtain some esters, with subsequent transesterification or, to obtain acids (R'=H), with subsequent hydrolysis in basic or acidic medium. In addition, the acids may be advantageously prepared by action of acetone-chloroform on compounds of the formula (III), in the presence of an alkali metal hydroxide.

As a modification, the compounds of the formula (I) in which R represents a $C_{1-5}$ alkyl group may be obtained from the unalkylated oximes (compounds of the formula (I) in which R=H) by reaction with an alkylating agent, in a manner known per se. Typically, said reaction may be effected with an alkyl halide in the presence of a base within a polar solvent.

However, the compounds of the formula (I) in which R is a $C_{1-5}$ alkyl radical are preferably prepared according to another modification from compounds of the formula (III), by reversing the order of the operating sequence. This results in a simplification of the purification steps at the various stages and, consequently, increased overall yields. Thus, this process comprises first reacting a compound of the formula (III) with a hydroxylamine of the formula $H_2NOR$ in which $R=C_{1-5}$ alkyl, to give a compound of the formula (V):

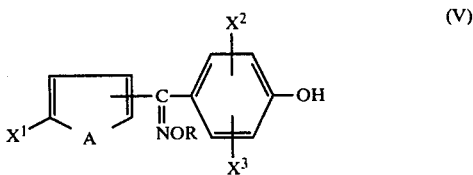

(V)

in which A, $X^1$, $X^2$ and $X^3$ have the above-defined meanings and R represents a $C_{1-5}$ alkyl group, and reacting the resulting compound of the formula (V) with a halogen-containing derivative of the formula (IV) or with an acetone-chloroform mixture in the presence of an alkali metal hydroxide.

The conditions for the reaction of compounds of the formula (III) with a hydroxylamine are the same as those used for reacting said hydroxylamine with compounds of the formula (II).

The conditions for the reactions by which compounds of the formula (V) give products of the formula (I) are the same as those used to prepare compounds of the formula (II).

The ketones of the formula (III) used as starting materials may generally be prepared by Friedel-Crafts reaction between heteroarylic acid chlorides and substituted anisoles, said reaction being followed by demethylation of the ether, with an acid, for example, or with pyridine hydrochloride.

When $X^2$ and/or $X^3$ represent halogen atoms, the product may also be prepared by reaction of chlorine, bromine or iodine with the compound of the formula (III) in which one at least of the radicals $X^2$ or $X^3$ represents hydrogen.

In following Table I are tabulated the characteristics of a number of such compounds of the formula (III), some of which are known compounds, together with the characteristics of the methyl ethers thereof.

TABLE I

| A | Position of C=O on the heterocycle | $X^1$ | $X^2$ | $X^3$ | R | M.P. °C. |
|---|---|---|---|---|---|---|
| S | 2 | H | 3-BR | H | $CH_3$ | 125 |
| S | 2 | H | 3-Br | H | H | 185 |
| S | 2 | H | H | H | $CH_3$ | 76 |
| S | 2 | H | H | H | H | 112 |
| S | 2 | H | 2-Cl | H | $CH_3$ | 64 |
| S | 2 | H | 2-Cl | H | H | 102 |
| S | 2 | H | 3-$CH_3$ | H | $CH_3$ | 50 |
| S | 2 | H | 3-$CH_3$ | H | H | 160 |
| S | 2 | H | 3-I | H | H | 194 |
| S | 2 | H | 3-Cl | H | $CH_3$ | 122 |
| S | 2 | H | 3-Cl | H | H | 174 |
| S | 2 | $CH_3$ | H | H | $CH_3$ | 73 |
| S | 2 | $CH_3$ | H | H | H | 133 |
| S | 2 | H | 2-$CH_3$ | 3-$CH_3$ | $CH_3$ | 76 |
| S | 2 | H | 2-$CH_3$ | 3-$CH_3$ | H | 144 |
| O | 2 | H | H | H | $CH_3$ | 65 |
| O | 2 | H | H | H | H | 164 |
| O | 3 | H | H | H | $CH_3$ | 75 |
| O | 3 | H | H | H | H | 135 |

The compounds described in the following Examples, to illustrate this invention, were studied from an analytical and a structural standpoint. The elemental analysis results confirm the empirical formula assigned; and the infrared (IR) and nuclear magnetic resonance (NMR) spectra confirm the structural formulae indicated; in mixtures of both isomers of the oxime function, the relative amounts thereof were determined from their proton NMR spectrum, in DMSO-$d_6$ solution at 60 M Hz.

EXAMPLE 1

Ethyl 2-[2-Bromo-4-(2-thienyl-hydroxyiminomethyl)-phenoxy]-2-methyl-propionate (A) Ethyl 2-[2-bromo-4-(2-thenoyl)-phenoxy]-2-methyl-propionate To a solution of 2-thienyl-(3-bromo-4-hydroxyphenyl)ketone (14.5 g; M.p.=185° C.) in dimethylsulfoxide (50 ml) is added potassium hydroxide (2.8 g) and the mixture is heated to 50° C. for 30 minutes, after which ethyl α-bromoisobutyrate (9.75 g) is added thereto at room temperature. After a period of time of 3 hours, the solution is poured into water (100 ml) and the aqueous phase is extracted with ethyl ether. The organic phase is washed with an aqueous sodium hydroxide solution, and then with water, and the solvent is evaporated off after drying over sodium sulfate. The final product is recrystallized from petroleum ether (7 g; M.p. = 80° C.).

(B) Ethyl 2-[2-bromo-4-(2-thenoyl)-phenoxy]-2-methyl-propionate (20 g) and hydroxylamine hydrochloride (15 g) are dissolved in pyridine (200 ml) and the mixture is refluxed for 5 hours, during which time two 3 g portions of hydroxylamine hydrochloride are added thereto. The pyridine is then removed under reduced pressure and the residue is dissolved in chloroform. The organic phase is washed with an aqueous hydrochloric acid solution, then with water, after which it is dried, the solvent is evaporated off and the final product is crystallized from petroleum ether or diisopropyl ether, to give 15 g of a mixture of the isomers of the oxime which has a melting point of 72° C. and which contains 70% of the isomer for which the chemical shift of the hydroxyl in the NMR spectrum is greater than for the other isomer, and which will be referred to as Isomer X.

EXAMPLE 2

2-[4-(2-Thienyl-hydroxyiminomethyl)phenoxy]-2-methyl propionic acid (A) Ethyl 2-[4-(2-thenoyl)-phenoxy]-2-methyl-propionate A mixture of 2-thienyl-(4-hydroxy-phenyl)ketone (M.p. 112° C.; 65 g), ethyl bromoisobutyrate (62 g) and potassium carbonate (88 g) in 2-butanone (500 ml) is refluxed for 24 hours. After removing the solid by filtration in the hot, the solvent is removed. The unreacted phenol is extracted from the residue with an alkaline aqueous solution. The usual treatments give, in a yield of 50%, the ester which melts at 45° C.

(B) 2-[4-(2-Thenoyl)-phenoxy]-2-methyl propionic acid

Ethyl 2-[4-(2-thenoyl)-phenoxy]-2-methyl-propionate (obtained in 2A; 11 g) is dissolved in aqueous ethanol (75:25; 100 ml); sodium hydroxide (1.5 g) is added thereto and the solution is heated to its reflux temperature for 1.5 hour. The ethanol is removed under reduced pressure and the aqueous solution is made acidic by addition of an inorganic acid. The final product precipitates out slowly, or may be extracted with ethyl ether, to give 7.5 g of acid which has a melting point of 157° C. (recrystallization from dichloroethane); said hydrolysis may be effected with other alkyline agents, for example with potassium hydroxide or potassium carbonate, without substantial change in the yields.

(C) The oximation is effected by submitting the compound obtained in Example 2B to the method described in Example 1B.

The resulting mixture of both stereoisomers Z/E melts at about 170° C.; its piperazine salt, prepared by action of one mole piperazine on two moles acid in ethanol, melts at 228° C. while the hydroxyethylamine salt melts at 180° C.

Pure isomer X (obtained, for example, by successive recrystallizations of the mixture from dichloroethane) which has a melting point of 188° C., is the isomer for which the greatest chemical shift for the hydroxyl of the oxime function is noted in the NMR spectrum. The sodium salt of said isomer, prepared by action of sodium hydroxide in aqueous medium and recrystallized from aqueous ethanol, forms a hydrate which melts above 260° C.

The other pure isomer (obtained, for example, by hydrolysis of the corresponding ester), isolated by chromatography, has a melting point of 190° C.

EXAMPLE 3

Ethyl 2-[4-(2-thienyl-hydroxyiminomethyl)-phenoxy]-2-methyl-propionate

Using the procedure described in Example 1, action of hydroxylamine hydrochloride on ethyl 2-[4-(2-thenoyl)-phenoxy]-2-methyl-propionate gives a mixture of the two oxime isomers, in a yield of 90%. Substantially the same result is obtained by refluxing for several hours an ethanol solution of ethyl 2-[4-(2-thenoyl)-phenoxy]-2-methyl-propionate and excess hydroxylamine hydrochloride, in the presence of one equivalent sodium acetate or barium carbonate.

The mixture, which has a melting point of 112° C. on recrystallization from ethanol, contains 85% isomer X which, on NMR analysis, exhibits a chemical shift of the N-substituted hydroxyl which is greater than that of isomer Y.

On recrystallization from ethanol-petroleum ether (50:50), the mixture of substantially equivalent amounts of both isomers melts at 100° C.

Pure isomer Y (separated from isomer X by column chromatography, for example) and after recrystallization from ethanol has a melting point of 128° C. Pure isomer X is obtained in excellent yields by isomerization of the mixture in anhydrous acidic medium; the reaction is preferably conducted in ethanol saturated with hydrochloric acid. On recrystallization from isopropyl ether, isomer X melts at 119° C.

EXAMPLE 4

Methyl 2-[4-(2-thienyl-hydroxyiminomethyl)-phenoxy]-2-methyl-propionate (A) Methyl 2-[4-(2-thenoyl)-phenoxy]2-methyl-propionate 2-[4-(2-Thenoyl)-phenoxy]-2-methyl-propionic acid (M.p. 157° C.; 29 g; obtained according to the procedure described in Example 2 from 2-thienyl(4-hydroxyphenyl)ketone) is dissolved in anhydrous methanol (300 ml), concentrated sulfuric acid (2 ml) is then added thereto and the mixture is heated for 6 hours at the reflux temperature. The solvent is then evaporated off under reduced pressure and the residue is dissolved in ethyl ether; the organic phase is washed with an aqueous sodium hydroxide solution. After neutralization and drying, the ether is evaporated off and the methyl ester is recrystallized from ethanol, to give 29 g of product which melts at 85° C.

(B) Using the procedure described in Example 1B, reaction of hydroxylamine hydrochloride with the previously described ketone gives the oxime having a melting point of 130° C., in a yield of 80%. The material is a mixture of both stereoisomers containing 65% type X isomer.

EXAMPLE 5

2-[4-(2-Furyl-hydroxyiminomethyl)-phenoxy]-2-methyl-propionic acid (A) 2-[4-(2-Furoyl)-phenoxy]-2-methyl-propionic acid 2-Furyl(4-hydroxy-phenyl)ketone (10 g) is dissolved in anhydrous acetone (80 g) and sodium hydroxide (13.2 g) is added thereto; the resulting mixture is stirred for 30 minutes after which anhydrous chloroform (20 g) is added dropwise thereto. On completion of the addition, the mixture is refluxed for 10 hrs. After cooling, the suspension is poured over 2 volumes water and the acetone is evaporated under reduced pressure. The aqueous phase is made acidic, and is then extracted with ethyl ether. The ether phase is neutralized, dried, and the solvent is evaporated off. The resulting solid is recrystallized from benzene, to give 9 g of acid which melts at 127° C. (B)

When the procedure described in Example 1B is applied to the preceding ketone, the acid/oxime is obtained as a mixture of both isomers having a melting point of 170° C., in a yield of 80%. The NMR spectrum discloses the presence of 80% type X isomer. When the content of X isomer is reduced to 65%, the mixture melts at 190° C., while the pure X isomer melts at 199° C. This compound may also be obtained by hydrolysis of ethyl 2-[4-(2-furyl-hydroxyiminomethyl)-phenoxy]-2-methyl-propionate, described in Ex. 6.

EXAMPLE 6

Ethyl 2-[4-(2-furyl-hydroxyiminomethyl)-phenoxy]-2-methyl-propionate (A) Ethyl 2-[4-(2-furoyl)-phenoxy]-2-methyl-propionate The compound is prepared according to the procedure described in Example 2A. This ester melts at 45° C.

(B) The ester obtained according to (A) (13 g) and hydroxylamine hydrochloride (15 g) in pyridine (50 ml) are refluxed for 5 hours; the pyridine is then removed under reduced pressure and the residue is dissolved in chloroform. The organic phase is washed with aqueous hydrochloric acid solutions, and then with water; the solvent is then evaporated under reduced pressure.

After drying the residue, the oxime/ester crystallizes as a mixture of both isomers having a melting point of 105° C.

The NMR spectrum discloses the presence of 70% type X isomer.

Isomerization of this mixture, to obtain the pure major isomer, is effected in ethanol or chloroform solution in the presence of anhydrous hydrochloric acid.

After recrystallization from ethanol or diisopropyl ether, the type X isomer melts at 110° C.

The compounds of the Examples shown in following Table II were prepared according to the same procedures as those described in Examples 1–6.

The ketones used as intermediates for the synthesis are tabulated in following Table III and characterized by their melting point.

TABLE II

| Example n° | Structural formula | % isomer X | % isomer Y | M.P. °C. |
|---|---|---|---|---|
| 7 | 2-thienyl-C(=NOH)-[phenyl(Cl)]-O-C(CH₃)₂-COOH | 60 | 40 | 89 |
| 8 | 2-thienyl-C(=NOH)-[phenyl(CH₃)]-O-C(CH₃)₂-COOH | 60 | 40 | 142 |
| 9 | 2-thienyl-C(=NOH)-[phenyl(I)]-O-C(CH₃)₂-COOH | 70 | 30 | 126 |
| 10 | 2-thienyl-C(=NOH)-[phenyl(Cl)]-O-C(CH₃)₂-COOH | 65 | 35 | 152 |
| 11 | 5-methyl-2-thienyl-C(=NOH)-phenyl-O-C(CH₃)₂-COOH | 70 | 30 | 188 |
| 12 | 2-thienyl-C(=NOH)-[phenyl(Br)]-O-C(CH₃)₂-COOH | 70 | 30 | 145 |
| 13 | 2-thienyl-C(=NOH)-phenyl-O-C(CH₃)₂-COOCH(CH₃)₂ | 70 | 30 | 90 |
| 13b | d° | 100 | — | 95 |

TABLE II-continued

| Example n° | Structural formula | % isomer X | % isomer Y | M.P. °C. |
|---|---|---|---|---|
| 14 | thiophene-C(=NOH)-C₆H₄-O-C(CH₃)₂-COOC₄H₉ | 80 | 20 | 75 |
| 15 | thiophene-C(=NOH)-[3-CH₃-C₆H₃]-O-C(CH₃)₂-COOC₂H₅ | 60 | 40 | 80 |
| 16 | thiophene-C(=NOH)-[3-I-C₆H₃]-O-C(CH₃)₂-COOC₂H₅ | 65 | 35 | 95 |
| 17 | thiophene-C(=NOH)-[3-Cl-C₆H₃]-O-C(CH₃)₂-COOC₂H₅ | 65 | 35 | 77 |
| 18 | thiophene-C(=NOH)-[2,3-(CH₃)₂-C₆H₂]-O-C(CH₃)₂-COOC₂H₅ | 65 | 35 | 108 |
| 19 | 5-CH₃-thiophene-C(=NOH)-C₆H₄-O-C(CH₃)₂-COOC₂H₅ | 70 | 30 | 98 |
| 20 | furan(3-yl)-C(=NOH)-C₆H₄-O-C(CH₃)₂-COOC₂H₅ | 100 | — | 113 |

TABLE III

| Structural formula | Intermediate ketones M.P. °C. |
|---|---|
| thiophene-CO-[3-Cl-C₆H₃]-O-C(CH₃)₂-COOH | 109 |
| thiophene-CO-[3-CH₃-C₆H₃]-O-C(CH₃)₂-COOH | 118 |
| thiophene-CO-[2,3-(CH₃)₂-C₆H₂]-O-C(CH₃)₂-COOH | 136 |
| 5-CH₃-thiophene-CO-C₆H₄-O-C(CH₃)₂-COOH | 140 |
| thiophene-CO-[3-Cl-C₆H₃]-O-C(CH₃)₂-COOH | 122 |
| thiophene-CO-[3-Br-C₆H₃]-O-C(CH₃)₂-COOH | 146 |

TABLE III-continued

| Structural formula | Intermediate ketones M.P. °C. |
|---|---|
| thiophene-CO-[3-I-C₆H₃]-O-C(CH₃)₂-COOH | 199 |
| thiophene-CO-[3,5-Br₂-C₆H₂]-O-C(CH₃)₂-COOH | 170 |
| thiophene-CO-C₆H₄-O-C(CH₃)₂-COOC₄H₉ | <50 |
| thiophene-CO-C₆H₄-O-C(CH₃)₂-COOCH(CH₃)₂ | 59 |
| thiophene-CO-[3-Cl-C₆H₃]-O-C(CH₃)₂-COOC₂H₅ | oil $n_D^{20}$ = 1.574 |
| thiophene-CO-[3-I-C₆H₃]-O-C(CH₃)₂-COOC₂H₅ | 84 |

TABLE III-continued

| Structural formula | M.P. °C. |
|---|---|
| Intermediate ketones | |
| thienyl-C(=O)-(Cl,CH₃-phenyl)-O-C(CH₃)₂-COOC₂H₅ | 65 |
| thienyl-C(=O)-(CH₃,CH₃-phenyl)-O-C(CH₃)₂-COOC₂H₅ | oil $n_D^{20} = 1.582$ |
| thienyl-C(=O)-(H₃C,CH₃,CH₃-phenyl)-O-C(CH₃)₂-COOC₂H₅ | oil |
| H₃C-thienyl-C(=O)-phenyl-O-C(CH₃)₂-COOC₂H₅ | 40 |
| (O-thienyl)-C(=O)-phenyl-O-C(CH₃)₂-COOC₂H₅ | 66 |

EXAMPLE 21

Butyl 2-[4-(2-thienyl-butoxyiminomethyl)-phenoxy]-2-methyl-propionate

2-[4-(2-Thienyl-hydroxyiminomethyl)-phenoxy]-2-methyl propionic acid (6.7 g) is dissolved in a sodium ethoxide solution in ethanol (100 ml; prepared from 1.3 g sodium), and the solution is then refluxed for 1 hour, after which dimethylformamide (75 ml) is added thereto and the ethanol is evaporated off. Butyl bromide (9 g) is added to the solution at 80° C. and the mixture is stirred for 3 hours, after which the solvent is evaporated under reduced pressure. Water and chloroform are then added to the resulting material. After stirring the mixture, the chloroform phase is decanted off and is then washed with an aqueous alkaline solution. After drying, the solvent is evaporated off and the desired ester is isolated as an oil consisting of an admixture of equivalent amounts of both stereoisomers Z/E. $n_d^{22} = 1.545$.

EXAMPLE 22

Ethyl 2-[4-(2-thienyl-ethoxyiminomethyl)-phenoxy]-2methyl-propionate

This compound, which is obtained as an oil, is prepared according to the procedure described in Example 21 and using ethyl bromide instead of butyl bromide. $n_D^{22} = 1.562$.

EXAMPLE 23

Ethyl 2-[4-(2-thienyl-methoxyiminomethyl)-phenoxy]-2-methyl-propionate

This oily compound, which consists of a mixture of both isomers Z/E, is obtained by reacting methyl iodide with ethyl 2-[4-(2-thienyl-hydroxyiminomethyl)-phenoxy]-2-methyl-propionate dissolved in dimethyl formamide and in the presence of potassium carbonate.

EXAMPLE 24

2-[4-(2-thienyl-methoxyiminomethyl)-phenoxy]-2-methyl-propionic acid.

2.4 g of ethyl ester obtained in Example 23 and 1.05 g potassium carbonate dissolved in 75% aqueous ethanol (25 ml) are maintained at 80° C. for 5 hours. The alcohol is then evaporated off, the resulting material is made acidic and the acid precipitate is filtered off, to give a mixture of equivalent amounts of both stereoisomers which melts at 168° C.

EXAMPLE 25

2-[4-(2-Thienyl-ethoxyiminomethyl)-phenoxy]-2-methyl-propionic acid

This compound is obtained by alkaline hydrolysis of the ethyl ester described in Example 22.

The mixture of both stereoisomers (containing 70% of the so-called isomer X) melts at 118° C., while pure isomer X (obtained by recrystallization from isopropyl ether) melts at 128° C.

EXAMPLE 26

2-[2-Methyl-4-(2-thienyl-methoxyiminomethyl)-phenoxy]-2-methyl-propionic acid (a)

2-Thienyl(4-hydroxy-3-methyl-phenyl)ketone(O-methyl oxime)

2-Thienyl(4-hydroxy-3-methyl-phenyl(ketone) (10 g) and methoxyamine hydrochloride (5 g) are dissolved in ethanol (120 ml) and pyridine (30 ml). The solution is maintained for several hours at its refluxing temperature, after which the solvents are removed under reduced pressure; the residual oil is taken up into a water-immiscible solvent. This organic phase is washed with aqueous acidic solutions, and then once with an aqueous sodium hydroxide solution to remove the unreacted ketone.

This gives the oxime (in a yield of 50%) as an admixture of both stereoisomers which melts at 98° C.

(b)

2-[2-Methyl-4-(2-thienyl-methoxyiminomethyl)-phenoxy]-2-methyl-propionic acid

Potassium hydroxide (2 g) is added to a solution (150 ml) of 9 g of the compound obtained in a) in dioxan; after ½ hour at the refluxing temperature of the solvent, ethyl 2-bromo-2-methyl-propionate is added thereto and refluxing is maintained for 5 hours. The inorganic precipitate is separated from the cooled solution and the solvent is removed under reduced pressure; the residual oil is dissolved in 60 ml aqueous ethanol (50:50) containing 2 g potassium hydroxide. The resulting material is heated 2 hours at the refluxing temperature; the ethanol is then removed, after which the solution is made acidic and the insoluble is extracted with a water-immiscible solvent, such as ethyl ether. The final acid is extracted with an aqueous sodium carbonate solution. After acidification of this aqueous phase, the acid is extracted therefrom with ethyl ether. It crystallizes after removal of the solvent, M.p = 108° C. (75% isomer X).

EXAMPLE 27

2-[4-(2-Furyl-propoxyiminomethyl)phenoxy]-2-methyl-propionic acid (a) 2-Furyl(4-hydroxy-phenyl)ketone-(O-propyl oxime)

To a solution of 9.4 g 2-furyl-(4-hydroxy-phenyl)ketone in 80 ml butanol is added propoxyamine hydrochloride (7.7 g) prepared according to methods known per se (M.p.=147° C.) and the mixture is heated to its refluxing temperature for about 12 hours. The solvent is then removed and the residue is dissolved in ethyl ether. The organic phase is washed with an aqueous acidic solution and then with water. The solvent is evaporated off and the residual oil is dissolved in benzene. The benzene phase is washed with an aqueous sodium carbonate solution and, after drying over sodium sulfate, the solvent is evaporated off, to give 11.1 g oxime (mixture of both stereoisomers) as an oil.

(b) 2-[4-(2-Furyl-propoxyiminomethyl-phenoxy]-2-methyl-propionic acid 11 g of the compound obtained in (a) are dissolved in 55 ml dimethylformamide; potassium carbonate (7.3 g) is added thereto, the mixture is then stirred for 1 hour, after which 10.3 g ethyl 2-bromo-2-methyl-propionate is added. The resulting mixture is stirred for several hours at room temperature and then at 80° C. It is then poured over 2 volumes water and extracted with ethyl ether. The ether phase is concentrated and the aliphatic esters are distilled off, to give an oil (13.2 g) which is dissolved in ethanol (130 ml) and water (30 ml) containing 4 g potassium hydroxide. The resulting material is refluxed for several hours, after which the ethanol is removed and the aqueous phase is treated as described in Example 1, to give, in a yield of 40%, a mixture of both stereoisomers of the acid which melts at 80° C. (60% isomer X).

EXAMPLE 28

2-[4-(2-Furyl-butoxyiminomethyl)-phenoxy]-2-methyl-propionic acid (a) 2-Furyl-(4-hydroxy-phenyl)ketone-(O-butyl oxime)

A solution of 2-furyl-(4-hydroxy-phenyl)ketone (50 g) and butoxyamine hydrochloride (36 g) in methanol (250 ml) is maintained 6 hours at its refluxing temperature. The solvent is then removed and the residue is dissolved in diisopropyl oxide (400 ml), the organic phase is washed with aqueous acidic and basic solutions and then with water. After drying the solution, the solvent is evaporated off, to give 46 g of oxime (mixture of both stereoisomers) having a melting point of 58° C. Separation of the isomers may be effected by fractional crystallization or by column chromatography through silica, using chloroform as eluent, for example.

(b) 2-[4-(2-Furyl-butoxyiminomethyl)-phenoxy]-2-methyl-propionic acid

To a solution of the compound obtained in (a) (10 g), in 2-butanone (100 ml) is added potassium carbonate (10.5 g); the mixture is heated to the refluxing temperature and ethyl 2-bromo-2-methyl-propionate (9.4 g) is then added thereto. After refluxing for 20 hours, the solid material is removed and the solvent is evaporated off. The residual oil is dissolved in 50% aqueous ethanol (80 ml) containing 4 ml concentrated aqueous sodium hydroxide solution. The mixture is maintained at 90° C. for 4 hours and the ethanol is then evaporated off. After acidification, the acid and residual phenol are extracted with diisopropyl oxide; the acid is in turn extracted with an aqueous sodium carbonate solution. Acidification of this material gives 6.5 g acid which is crystallized from petroleum ether.

This compound, which is a mixture of both stereoisomers of the oxime and which melts at 62° C. contains about 70% type X isomer.

Recrystallizations from ethanol-petroleum ether (50:50) give a pure isomer which melts at 120° C.; the other isomer is separated by chromatography and melts at 71° C.

(c) The acid obtained in (b) may also be prepared by action of an acetone-chloroform-potassium hydroxide mixture on the compound obtained in (a).

To a solution of the compound obtained in (a) (10 g) in acetone (150 ml) is slowly added ground potassium hydroxide (25 g) followed by the dropwise addition of chloroform (12.6 ml). After refluxing for 2 hours, the mixture is poured over 2 volumes water, neutralized, and the solvents are evaporated off, after which the final acid is extracted with diisopropyl oxide. Purification gives 8 g of acid.

The compounds of the Examples set forth in Table IV were prepared according to the procedures of Examples 26–28.

TABLE IV

| Example n° | Structural formula | M.p. °C. | % X |
|---|---|---|---|
| 29 | furyl-C(=NOC2H5)-C6H4-O-C(CH3)2-COOH | 95 | 65 |
| 30 | furyl-C(=NOC2H5)-C6H3(Cl)-O-C(CH3)2-COOH | 90 | 60 |
| 31 | furyl-C(=NOC2H5)-C6H3(Br)-O-C(CH3)2-COOH | 92 | 65 |
| 32 | furyl-C(=NOC3H7)-C6H3(Br)-O-C(CH3)2-COOH | 110 | 0 |
| 33 | furyl-C(=NOC4H9)-C6H3(Br)-O-C(CH3)2-COOH | 110 | 0 |
| 34 | thienyl-C(=NOCH3)-C6H3(Cl)-O-C(CH3)2-COOH | 141 | 80 |
| 35 | furyl-C(=NOCH3)-C6H4-O-C(CH3)2-COOH | 169 | 70 |

TABLE IV-continued

| Example n° | Structural formula | M.p. °C. | % X |
|---|---|---|---|
| 36 | (furan)-C(=NOCH3)-(phenyl)-O-C(CH3)2-COOC2H5 | 58 | 95 |

The results of pharmacological tests reported hereinafter demonstrate the usefulness of compounds of the formula (I) as hypocholesterolemic, hypolipemic and uricosuric agents.

All the compounds have little toxicity, since the oral $LD_{50}$ in mice is generally in excess of 1000 mg/kg. The method used for the determination is that disclosed by C. I. BLISS, Quart. J. Pharm. Pharmacol., 2, 192–216 (1938). The ketones of the formula (II) have $LD_{50}$ values of the same order of magnitude as those of the oxime; this is also the case with ethyl 4-chloro-phenoxyiso-butyrate (Clofibrate).

The hypocholesterolemic activity of the compounds of the formula (I) was evidenced in normal mice and in mice whose cholesterolemia was increased by means of a Triton injection; three doses of the test compounds were orally administered to the animals within 48 hours, the cholesterol blood level being determined 24 hours after the last administration.

The results obtained with representative compounds of this invention and with the ketones from which they are derived are reported in following Table V, and compared with those obtained with ethyl 4-chloro-phenoxyisobutyrate (Clofibrate).

TABLE V

| Compound of Example n° | Unit dose mg/kg | Percent variation of the cholesterol level with respect to the untreated animals | |
|---|---|---|---|
| | | Normal mice | Mice having been given a Triton injection |
| 2 | 50 | −31.9⊕ | −33.4 |
| | 25 | −21.1⊕ | −38.3⊕ |
| (ketone corresponding to 2) | 200 | −21⊕ | −32⊕ |
| 3 | 25 | −39.3⊕ | −65⊕ |
| (isomer Y) | 5 | −29.8⊕ | −51.1⊕ |
| | 2 | −12.2⊕ | −41.8⊕ |
| 12 | 100 | −12.6⊕ | −60.7⊕ |
| | 50 | +6.8 | −40 |
| 11 | 50 | −19⊕ | −49⊕ |
| 5 | 200 | −40⊕ | −60⊕ |
| | 100 | −24⊕ | −20⊕ |
| | 10 | −37⊕ | −28⊕ |
| (ketone corresponding to 5) | 200 | +4.6 | −21 |
| 6 | 100 | −27⊕ | −47⊕ |
| | 25 | −2.6 | −29⊕ |
| 22 | 100 | −26⊕ | −47⊕ |
| | 50 | −26⊕ | −59⊕ |
| 21 | 100 | −27.7⊕ | −50.6 |
| | 50 | −21.9⊕ | −49⊕ |
| 28 | 5 | −15⊕ | −56⊕ |
| 36 | 100 | −33⊕ | −50⊕ |
| | 10 | −26⊕ | −26⊕ |
| Clofibrate | 400 | −24.8 | −23.3 |

⊕Results statistically significant for P <0.05

The activity on uric acid of compounds of the formula (I), particularly of the compounds of the formula (I) in which R'=H, was evidenced in rat, by the study of the urinary retention of phenol red, a method disclosed by H. C. SCARBOROUGH, G. R. McKIN-NEY, J. Med. Pharmaceutical Chem., 5, 175 (1962) and by E. KREPPEL, Med. Exptl., 1, 285 (1959).

This test is not a dosage of uric acid, which is impossible to effect in rodents, but a study of the elimination rate of phenol red, a known compound, from the blood of rats, after I.V. administration to the animals. It is known that when rats are administered known uricosuric compounds such as 2-ethyl-3-benzofuranyl 4-hydroxy-3,5-diiodo-phenyl ketone, 4-(dipropyl-sulfamoyl)benzoic acid or 1,2-diphenyl-4-[2-(phenyl-sulfinyl)ethyl]-3,5-pyrazolidinedione, prior to phenol red administration, the elimination rate of this dye decreases.

In following Table VI are reported results obtained with compounds of the formula (I) which show that the uricosuric activity may be superior to that of benziodarone (non-appropriated international name) which is commonly used for therapeutic purposes in humans.

TABLE VI

| Compound of Example n° | Dosage mg/kg | Percent retention of phenol red with respect to the untreated animals | | | |
|---|---|---|---|---|---|
| | | After 15 mn | After 30 mn | After 45 mn | After 60 mn |
| 12 | 100 | +81⊕ | +100⊕ | +100⊕ | +77⊕ |
| 10 | 100 | +65⊕ | +110⊕ | +79⊕ | +100⊕ |
| 5 | 100 | +27.3⊕ | 28.6⊕ | +25 | +30 |
| 19 | 100 | +47⊕ | +42⊕ | +34⊕ | +29⊕ |
| 21 | 100 | +25.6⊕ | +27.7⊕ | +20⊕ | +13.6⊕ |
| Benziodarone | 100 | +37⊕ | +50⊕ | +53⊕ | −18 |

⊕Results statistically significant for P <0.05

Two stereoisomers corresponding to the same structural formula exhibit qualitatively the same pharmacological activities, although their $ED_{50}$ values are generally different.

The compounds of the formula (I) and the salts of acids of the formula (I) with physiologically acceptable bases are useful in the treatment of hypercholesterolemia and hyperlipemia, whether or not associated with hyperuricemia, or in the treatment of hyperuricemia.

Thus, this invention relates also to therapeutic compositions comprising a therapeutically effective dosage of a compound of the formula (I) or of a salt of an acid of the formula (I) with physiologically acceptable bases, typically in admixture with a pharmaceutically acceptable excipient.

Said compositions may be administered to humans by the oral route, formulated as capsules, tablets or solutions, at a daily dosage regimen of 1–200 mg.

Having now described our invention what We claim as new and desire to secure by Letters Patent is:

1. A compound selected from the group consisting of compounds of the formula:

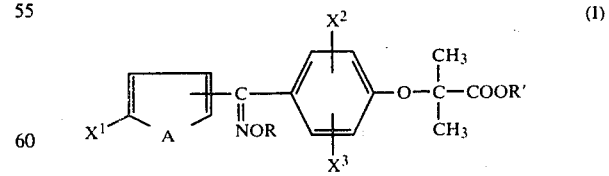

(I)

which represents a compound selected from the isomer Z, the isomer E and mixture of both stereoisomers of the oximino group and in which:

A is selected from oxygen and sulfur,
$X^1$ is selected from halogen, hydrogen and methyl,
R is selected from hydrogen and $C_{1-5}$ alkyl, $X^2$ and $X^3$, which may be the same or different, are each selected from hydrogen, halogen and $C_{1-5}$ alkyl, R' is selected from hydrogen and $C_{1-5}$ alkyl, the group

is at a position selected from 2- and 3-position on the heterocycle, the salts of the acids of the formula (I) with physiologically acceptable bases, and the compounds which are metabolically converted to compounds of the formula (I).

2. A compound as claimed in claim 1, wherein R is $C_{1-5}$ alkyl.

3. A compound as claimed in claim 2, wherein $X^2$ and $X^3$ are hydrogen atoms.

4. A compound selected from 2-[4-(2-furyl-propoxyiminomethyl)-phenoxy]-2-methyl-propionic acid, its stereoisomers Z and E, mixtures of said stereoisomers, its salts with physiologically acceptable bases and its $C_{1-5}$ alkyl esters.

5. A compound selected from 2-[4-(2-furyl-butoxyiminomethyl)-phenoxy]-2-methyl-propionic acid, its stereoisomers Z and E, mixtures of said stereoisomers, its salts with physiologically acceptable bases and its $C_{1-5}$ alkyl esters.

* * * * *